United States Patent [19]

Zachariades

[11] Patent Number: 4,944,974

[45] Date of Patent: Jul. 31, 1990

[54] COMPOSITE STRUCTURES OF ULTRA-HIGH-MOLECULAR-WEIGHT POLYMERS, SUCH AS ULTRA-HIGH-MOLECULAR-WEIGHT POLYETHYLENE PRODUCTS, AND METHOD OF PRODUCING SUCH STRUCTURES

[76] Inventor: Anagnostis E. Zachariades, 65 Glengary Way, Hillsborough, Calif. 94010

[21] Appl. No.: 262,970

[22] Filed: Oct. 26, 1988

Related U.S. Application Data

[63] Continuation-in-part of Ser. No. 132,200, Dec. 14, 1987, abandoned, which is a continuation-in-part of Ser. No. 936,838, Dec. 2, 1986, abandoned, which is a continuation-in-part of Ser. No. 811,015, Dec. 18, 1985, Pat. No. 4,655,769.

[51] Int. Cl.$^5$ .................. B32B 27/00; B32B 27/12
[52] U.S. Cl. .................. 428/36.1; 428/36.4;
   428/36.91; 428/252; 428/286; 428/290;
   428/298; 428/500; 428/515; 428/902; 428/911
[58] Field of Search .................. 428/500, 515, 902

[56] References Cited

U.S. PATENT DOCUMENTS

| | | | |
|---|---|---|---|
| 4,109,543 | 8/1978 | Foti | 428/252 |
| 4,403,012 | 9/1983 | Harpell et al. | 428/286 |
| 4,413,110 | 11/1983 | Kavesh et al. | 524/462 |
| 4,457,985 | 7/1984 | Harpell et al. | 428/911 |
| 4,518,647 | 5/1985 | Morrison | 428/252 |
| 4,737,402 | 7/1988 | Harpell et al. | 428/286 |

FOREIGN PATENT DOCUMENTS 2133740  8/1984  United Kingdom .

Primary Examiner—Ellis P. Robinson
Assistant Examiner—Archene A. Turner
Attorney, Agent, or Firm—Owen, Wickersham & Erickson

[57] ABSTRACT

A single-phase composite structure of filamentary and non-filamentary semicrystalline morphology made from the same polymer, which is of a type capable of gelling in a suitable solvent and of being deformed into a high-modulus, high-strength product. Layers of the polymer in sheet form are interleaved with at least one layer, also of that polymer, made from filaments thereof. The method of making the product may involve heating a sheet of UHMWPE or other polymer gel (5% UHMWPE in 95% paraffin oil, by weight) to 125° C., applying a knitted UHMWPE high modulus, high-strength structure on one side thereof, extracting the non-volatile paraffin oil therefrom with hexane, and evaporating the hexane.

17 Claims, 4 Drawing Sheets

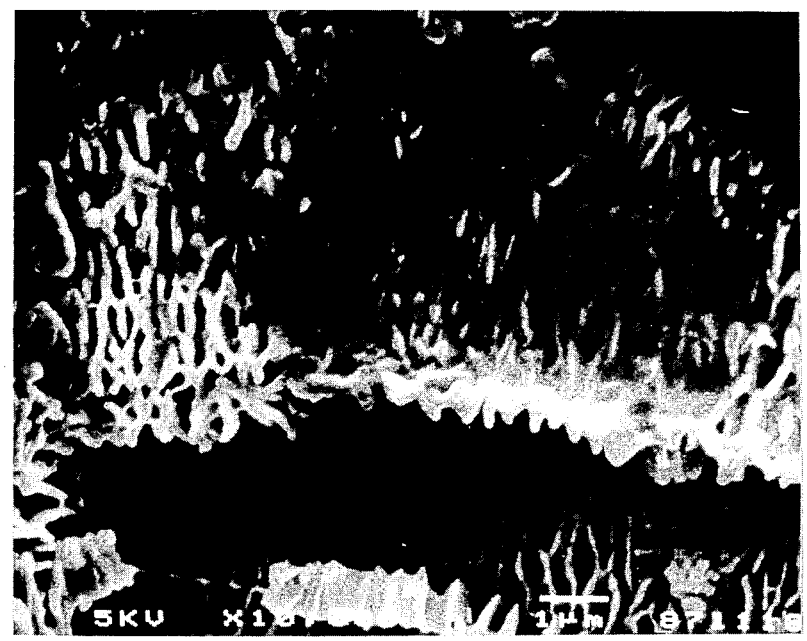
FIG._1
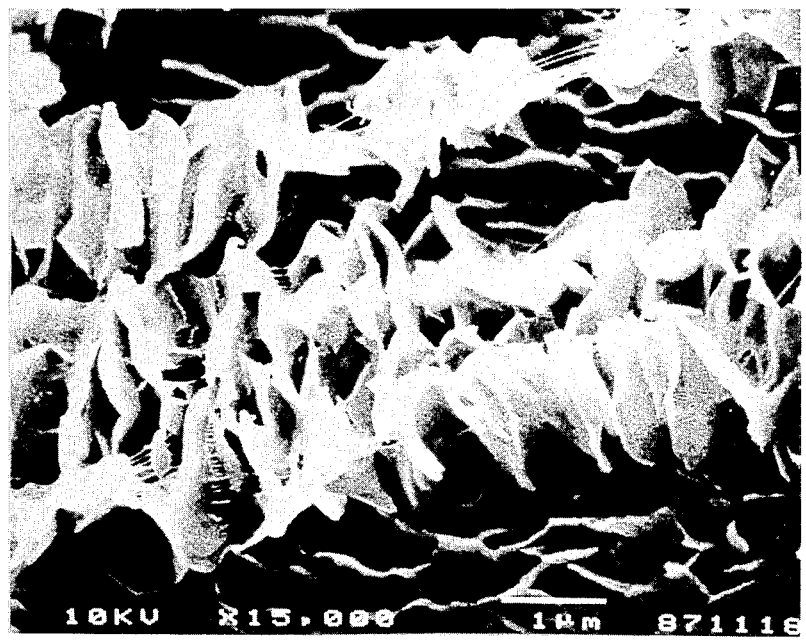
FIG._2

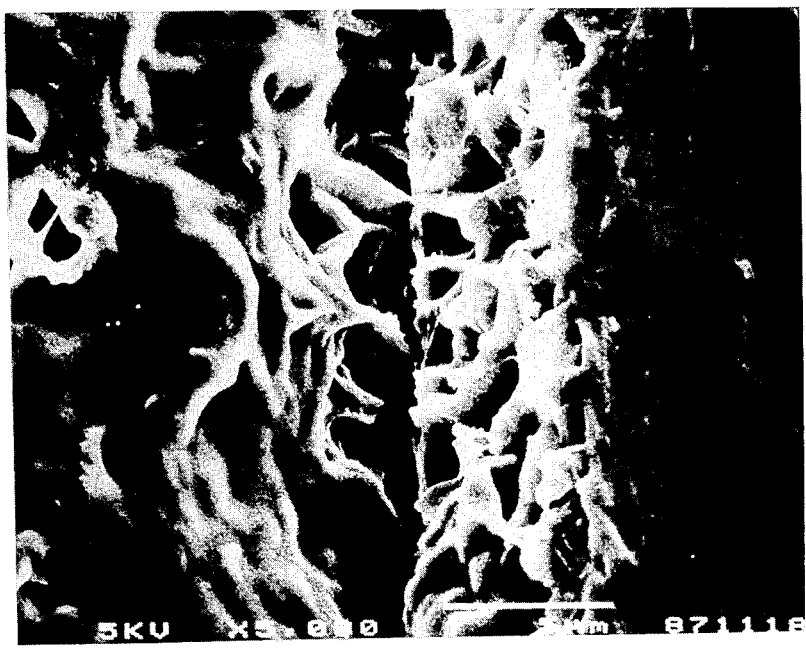
FIG._3

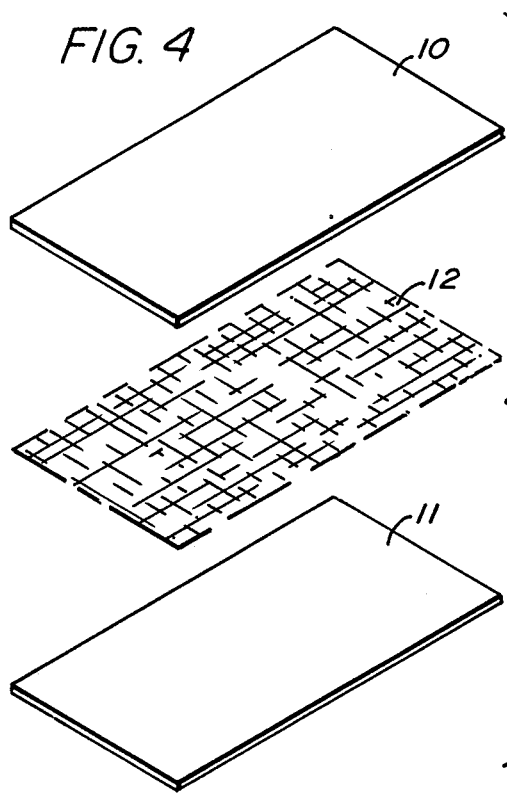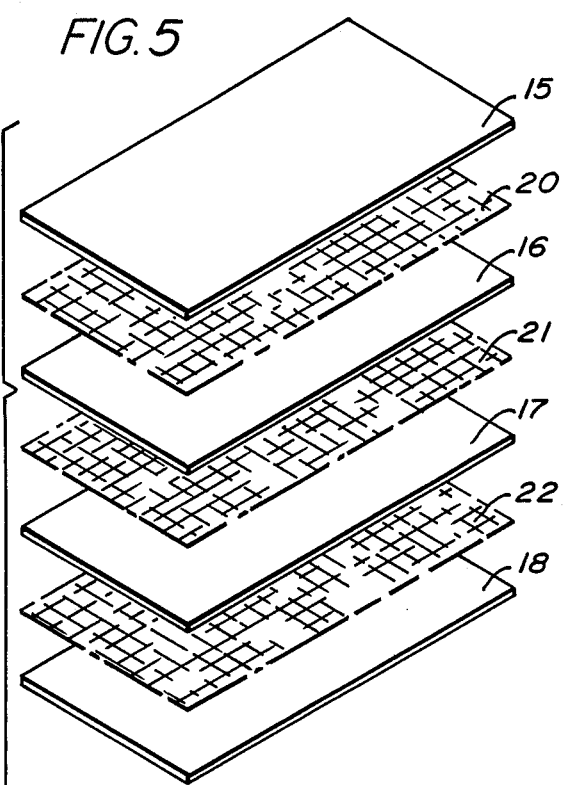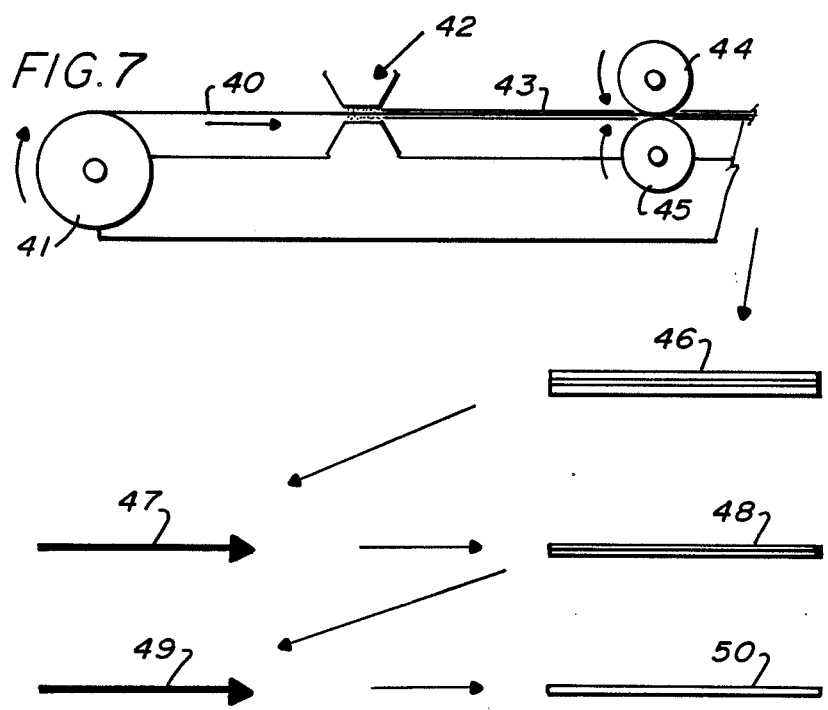

COMPOSITE STRUCTURES OF ULTRA-HIGH-MOLECULAR-WEIGHT POLYMERS, SUCH AS ULTRA-HIGH-MOLECULAR-WEIGHT POLYETHYLENE PRODUCTS, AND METHOD OF PRODUCING SUCH STRUCTURES

REFERENCE TO RELATED PATENT APPLICATION

This application is a continuation-in-part of U.S. Pat. application Ser. No. 132,200, filed Dec. 14, 1987, now abandoned which was a continuation-in-part of U.S. Pat. application Ser. No. 936,838 filed Dec. 2, 1986, now abandoned, which was a continuation-in-part of U.S. Pat. application Ser. No. 811,015, filed Dec. 18, 1985, now U.S. Pat. No. 4,655,769, to which reference may be made as to details described there.

SPECIFICATION

This invention relates to composite structures of ultra-high-molecular-weight polymers, as for example, polyethylene (UHMWPE) composites, of both filamentary and non-filamentary semicrystalline morphologies. In the composite structure of this invention the matrix and its fiber reinforcement are comprised of the same polymer resin, as for example, an ultra-high-molecular weight polyethylene, or of polymer resins with similar properties. Such composite structures are prepared by a processing methodology that includes the gelation of the matrix components on the reinforcing fibrillar component and the subsequent extraction or evaporation of the solvent that is incorporated initially in the matrix from the composite.

BACKGROUND OF THE INVENTION

The parent application, now U.S. Pat. No. 4,655,769, describes and claims a pseudo-gel comprising a suitable solvent in an amount of 99 to 90 percent by weight and an ultra-high-molecular-weight polymer such as polyethylene (UHMWPE) in an amount of 1 to 10 percent by weight. The pseudo-gel of the ultra-high-molecular weight polymer, e.g. an ultra-high-molecular-weight polyethylene, is a semicrystalline network with adjustable crystalline morphology comprising randomly dispersed and oriented chain-folded single crystals, stacks of single crystals, spherulitic crystals, and extended-chain shish-kebab-type of fibrils with lengths up to a few millimeters and widths up to 20 μm. The semicrystalline ultra-high-molecular-weight polymer, such as polyethylene, is obtained by removal of the solvent from the pseudo-gel. The application also describes a method for making a pseudo-gel precursor and a ultra-high-molecular-weight polyethylene product.

Near the end of that application, reference is made to composite structures of UHMWPE filamentary and non-filamentary semicrystalline morphologies. The present invention relates to such composite structures and to the processing methodology relating thereto.

FABRICATING COMPOSITES

The fabrication of composites from the same polymer, that is, composites in which both the matrix and the reinforcing fibers are comprised of the same polymer, e.g., polyethylene, has been possible both when using different morphologies of the polyethylene, one as a matrix and another as a reinforcing fiber, and also when using different types of polyethylene, one as a matrix and another type as a reinforcing fiber. In either case, the underlying principle is that the polyethylene matrix component is transcrystallized from the melt state on the polyethylene reinforcing fiber; this process is critically dependent on the difference of the melting temperatures of the polyethylene matrix component and the polyethylene reinforcing fiber component of the same polymer composite system. Thus, for example, for high density polyethylene with weight-average molecular weight of about 60,000, the melting point of the unprocessed (as received) resin pellets is about 132° C. and the melting point of the high-modulus and high-strength fibers of the same polymer resin produced by solid state deformation is about 138° C. This melting point difference of only about 6° has been utilized for the fabrication of a single-phase composite, but it is far too small for the practical and commercial fabrication of a single phase composite of this polyethylene with high tensile modulus and high-strength performance using this particular methodology, i.e., by transcrystallization from the melt state on to the polyethylene reinforcing fiber because of the partial melting of the fibers during the transcrystallization of the matrix on them, which resulted in the deterioration of their properties and consequently of the properties of the composite. One way to alleviate this processing difficulty is to use polyethylenes of different types, i.e., a low-density polyethylene or a low or high density polyethylene copolymer as a matrix component and a high-density polyethylene as a reinforcing fiber component with their respective melting points significantly different, so that the transcrystallization of the polyethylene matrix component from the melt state can occur without the deterioration of the mechanical properties of the polyethylene fiber component. Prior art shows the use of this approach with the fabrication of a composite of a low density polyethylene as a matrix and a high density polyethylene as the reinforcing fiber. However, these polyethylenes have physical and mechanical properties different from each other, in particular, melting temperatures, as the melting temperature of the low density polyethylene is 98°–115° C. and of the high density polyethylene 130°–137° C. Also the low density polyethylene is a branched polymer whereas the high density polyethylene is a linear polymer. For example, U.S. Pat. No. 4,457,785 shows the molding of low-density polyethylene and high-density polyethylene fibers into a polyethylene composite structure. Also, the same patent shows the molding of a copolymer of high-density polyethylene and ethylene hexane-1 with high-density polyethylene fibers. Similarly, a composite of a single polymer can be prepared by using a matrix of high-density polyethylene having a weight average molecular weight of (e.g.) 60,000 and a melting temperature of about 130° C. to 138° C. and a reinforcing fiber component of ultra-high-molecular-weight polyethylene (e.g., $M_w > 3 \times 10^6$) with a melting temperature of about 142° C., by transcrystallizing the low-molecular weight polyethylene matrix component from the melt onto the fibers; but again such a single-polymer composite is composed of very different types of polyethylenes, and it is formed by transcrystallizing the low-molecular weight polyethylene from the melt state onto the ultra-high-molecular weight polyethylene fibers. The low-molecular-weight polyethylene is readily melt-processable, whereas for all practical purposes the ultra-high-molecular-weight does not have a measurable melt-flow index. The very high molecular weight (several million) of the ultra-high-molecular-weight polyethylene gives it unique properties and processing characteristics which are not encountered in the normal high-density polyethylenes (e.g., high-density polyethylene resins with molecular weights up to about 300,000–400,000). Thus the preparation of a composite structure by the process of melt crystallizing the matrix on the reinforcing fibers using the same UHMWPE resin as a matrix and fiber (e.g., an UHMWPE resin with weight average molecular weight greater than $3 \times 10^6$) is not possible for two basic reasons:

(1) The UHMWPE at its melting temperature ($T_m \sim 138°$) does not flow to coat the UHMWPE fibers as it would have happened with a high-density polyethylene resin having a low weight-average molecular weight, e.g., Mw 60,000–300,000, and (2) the melting temperature of the UHMWPE in the matrix ($T_m \sim 138°$ C.) and fiber ($T_m \sim 142°$ C.) form are very close, and the use of the melt-crystallization approach leads to the deterioration of the mechanical properties of the reinforcing fibers because of their partial or complete melting. Therefore, it is apparent that the prior art teaches that single-phase composites can be fabricated only by using dissimilar resins and that such composites are comprised of a melt-crystallized matrix into the reinforcing fibers. In addition, it becomes important to notice that unless the polyethylenes used as the matrix and those used as the reinforcing fiber are of different types and have melting points that are significantly different, the fabrication of single-phase composites in which the matrix and the reinforcing fiber are composed of the same polymer resin or from polymer resins with identical or similar properties prior to their processing into the matrix and fiber forms, is impractical when using the teachings of the prior art.

Thus, an object of this invention is the fabrication of a single-phase composite without the transcrystallization of the matrix from the melt on the reinforcing fibers, by using a methodology which involves the gelation of the matrix component on the reinforcing fiber component and the subsequent removal of the solvent from the matrix (by extraction or evaporation, depending on the volatility of the solvent) while it is incorporated into the composite structure.

A key issue in the use of this methodology, shown clearly in the parent patent (U.S. Pat. No. 4,655,769) is that the pseudo gel of an ultra-high-molecular-weight polyethylene has a melting temperature ($T_m \sim 123°$ C.) which is substantially lower than the semicrystalline morphology which is produced after the removal of the solvent; as shown in Table I in Col. 7 of the parent patent, the melting temperature of the semicrystalline UHMWPE morphology is $\sim 137°$ C. i.e., $\sim 14°$ C. greater from the $T_m$ of the pseudo-gel in paraffin oil ($T_m \sim 123°$). Considering that the melting temperature of the highly oriented fibers made of the same UHMWPE resin is $\sim 142°$–$145°$ C., there is a temperature difference of $\sim 20°$ C. between the $T_m$ of the pseudo-gel of UHMWPE in paraffin oil and the UHMWPE fibers for forming a single phase composite by gelling a polymer resin onto itself in another state, i.e., as fiber. This substantial temperature drop of the melting temperature of the UHMWPE which is attained by the formation of the pseudo-gel state has the important implication that one can take any polymer resin that is capable of gelling and apply it at the melting temperature of the crystals in the gel as matrix on a fiber of the same polymer resin or of the same polymer. The term pseudo-gel refers to a concentrated solution of organic polymer which contains an entangled three-dimensional semicrystalline network the morphology of which may vary with the conditions of preparation or crystallization.

Polymer resins which can be used with the methodology of this disclosure must be capable of (a) forming a pseudo-gel state as described in the parent U.S. Pat. No. 4,655,769, and (b) being deformed into high-modulus high-strength fibrous products.

Polymers which meet these requirements must be linear and have a very high molecular weight, such as ultra-high-molecular-weight polyethylene (UHMWPE), or polar groups in the chain backbone, such as the polyamides.

By polymer having a very high molecular weight, it is meant, a polymer resin having a weight average molecular weight of at least 500,000 and preferably above two million.

Another object of this invention is the fabrication of a single phase composite in which the matrix has a different crystalline morphology from the melt crystallized morphology of the matrix components used in prior art (references—U.S. Pat. Nos. 4,737,402; 4,457,985; 4,403,012).

Another object of this invention is the fabrication of a single-phase composite structure in which the matrix and the reinforcing fibers are of the same polymer resin.

Another object of this invention is the fabrication of a single-phase composite in which the matrix and the reinforcing fibers are from resins with identical or similar properties prior to their processing into the matrix and the reinforcing fiber.

For example, a system of a matrix and reinforcing fibers of the same UHMWPE resin, e.g., an UHMWPE with weight average molecular weight $>3 \times 10^6$, is a single phase composite falling under the scope of this invention because:

(a) the matrix and the reinforcing fibers comprising the composite are products of the same UHMWPE polymer resin obtained by independent fabrication processes. If UHMWPEs of different manufacturers are used, one for the matrix and the other for the reinforcing fiber component, such a composite system falls also under the scope of this invention because UHMWPE as defined by ASTM are those "linear polyethylenes which have a relative viscosity of 2.3 or greater, at a solution concentration of 0.05% at 135° C. decahydronaphthalene", (Decalin) i.e., having a weight-average molecular weight of at least $3.1 \times 10^6$;

(b) the UHMWPE forms a pseudo-gel state in a solvent such as paraffin oil or decahydronaphthalene (the capability to form a pseudo-gel associates with the high molecular weight of the UHMWPE);

(c) UHMWPE is a linear polymer; and (d) UHMWPE can be fabricated into a high-modulus and high-strength fibrous product.

Similarly, the single phase composites in which the matrix and the reinforcing fibers might be composed of UHMWPE resins of different manufacturers, and single-phase composites in which the matrix and the reinforcing fiber components are comprised of linear polymer resins with the same chemical structure and identical or similar properties prior to their fabrication into a matrix and reinforcing fibers, are included in the scope of the invention.

Other polymers which can be used under the scope of the invention include polymers such as isotactic polypropylene, poly(L-lactide), poly(vinyl alcohol), polyacrylonitrile, poly(ethylene terephthalate) and polyamides. Solvents which may be used for dissolving and forming pseudo-gels with these polymers are, Decalin (decahydronaphthalene) and paraffin oil for polypropylene, chloroform for poly(L-lactide), ethylene glycol and water for poly(vinyl alcohol), dimethyl formamide and tetramethylene sulfone for polyacrylonitrile, nitrobenzene for poly(ethylene terephthalate), and benzyl alcohol for the polyamides.

SUMMARY OF THE INVENTION

A single-phase composite according to this invention is one in which the matrix and the reinforcing fibers are of the same polymer resin or from polymer resins with identical or similar properties prior to their processing into the matrix and fiber components of the composite.

Polymers which can be used in the invention include polyethylene and polymers such as isotactic polypropylene, poly(L-lactide), poly(vinyl alcohol), polyacrylonitrile, poly(ethylene terephthalate), and polyamides. Solvents which may be used for dissolving and forming pseudo-gels with these polymers are Decalin and paraffin oil for polypropylene, chloroform for poly(L-lactide), ethylene glycol and water for poly(vinyl alcohol), dimethyl formamide and tetramethylene sulfone for polyacrylonitrile, nitrobenzene for poly(ethylene terephthalate), and benzyl alcohol for the polyamides.

The feasibility of fabricating a single-phase composite within the scope of this invention is based on the idea that the melting temperature of the crystals in the pseudo-gel state of a semicrystalline polymer in a suitable solvent is significantly lower than the melting point of the semicrystalline polymer proper. In the case of UHMWPE, the crystals in the pseudo-gel of UHMWPE in paraffin oil melt at approximately 120° C., depending on the preparation conditions, whereas a semicrystalline morphology of the same polymer obtained from the gel-precursor (after solvent extraction) has a melting point of 130°-137° C. and even higher, above 140° C., after its drawing into a fibrillar structure.

Thus, the UHMWPE pseudo-gel can be applied in a temperature range below 130° C. on UHMWPE drawn fibers without affecting the mechanical performance of the fibers. The processing temperature for the single phase composite can be extended to lower limits (100° C. or lower), depending on the concentration and the preparation conditions of the pseudo-gel state; however, it is preferred that the temperature be close to or above the melting temperature of the crystals in the pseudo-gel, so that the latter can flow more readily and wet the reinforcing fibers for better bonding between the matrix and the fibers. Upon cooling to ~120° C., the pseudo-gel is formed onto the reinforcing fibers which, as discussed in the parent patent is comprised of a continuous molecular network of crystals. After solvent extraction or evaporation, the composite is comprised of only the residual semicrystalline UHMWPE matrix on the UHMWPE fibers. This process is substantially different from the melt processing of the prior art for fabricating composite structures. For example, in the melt-process, the matrix is a solid (no solvent(s) is present) which is heated to melt flow around the reinforcing fibers (in contrast to forming a solution in our case), and subsequently cooled to crystallize onto the fibers by melt crystallization (instead by gelation as the present process). Also, the rheological behavior of the matrix as a melt is distinctly different from the "solid-like" pseudo-gel behavior of the matrix of the present process.

The reinforcing fibers can be continuous in some particular direction, dispersed randomly, and knitted or woven in some particular pattern.

BRIEF DESCRIPTION OF THE DRAWINGS

FIG. 1 is an electron micrograph showing a deposited layer of UHMWPE matrix on the crystalline reinforcing UHMWPE fibers. The magnification is 10,000×, and the dimension of one micrometer is shown by the white bar.

FIG. 2 is an electron micrograph showing "shish-kebab" crystals of the UHMWPE matrix onto the crystalline lamellar structure of the UHMWPE reinforcing fibers. The magnification is 15,000×, and the dimension of a micrometer is shown by the white bar.

FIG. 3 is an electron micrograph showing two adjacent and aligned UHMWPE reinforcing fibers with their characteristic crystalline lamellar structure partially covered by the UHMWPE matrix. The magnification is 5,000×, and the dimension of one micrometer is shown by the white bar.

FIG. 4 is an exploded, diagrammatic view in perspective of a composite laminated structure embodying the principle of this invention and having a single knitted fibrillar structure between two pseudo-gel sheets.

FIG. 5 is a similar view of a multilayer composite structure according to this invention.

FIG. 7 is another flow sheet with diagrammatic views illustrating a process of the invention for making a flat structure.

DESCRIPTION OF SOME PREFERRED EMBODIMENTS

Figure 6:
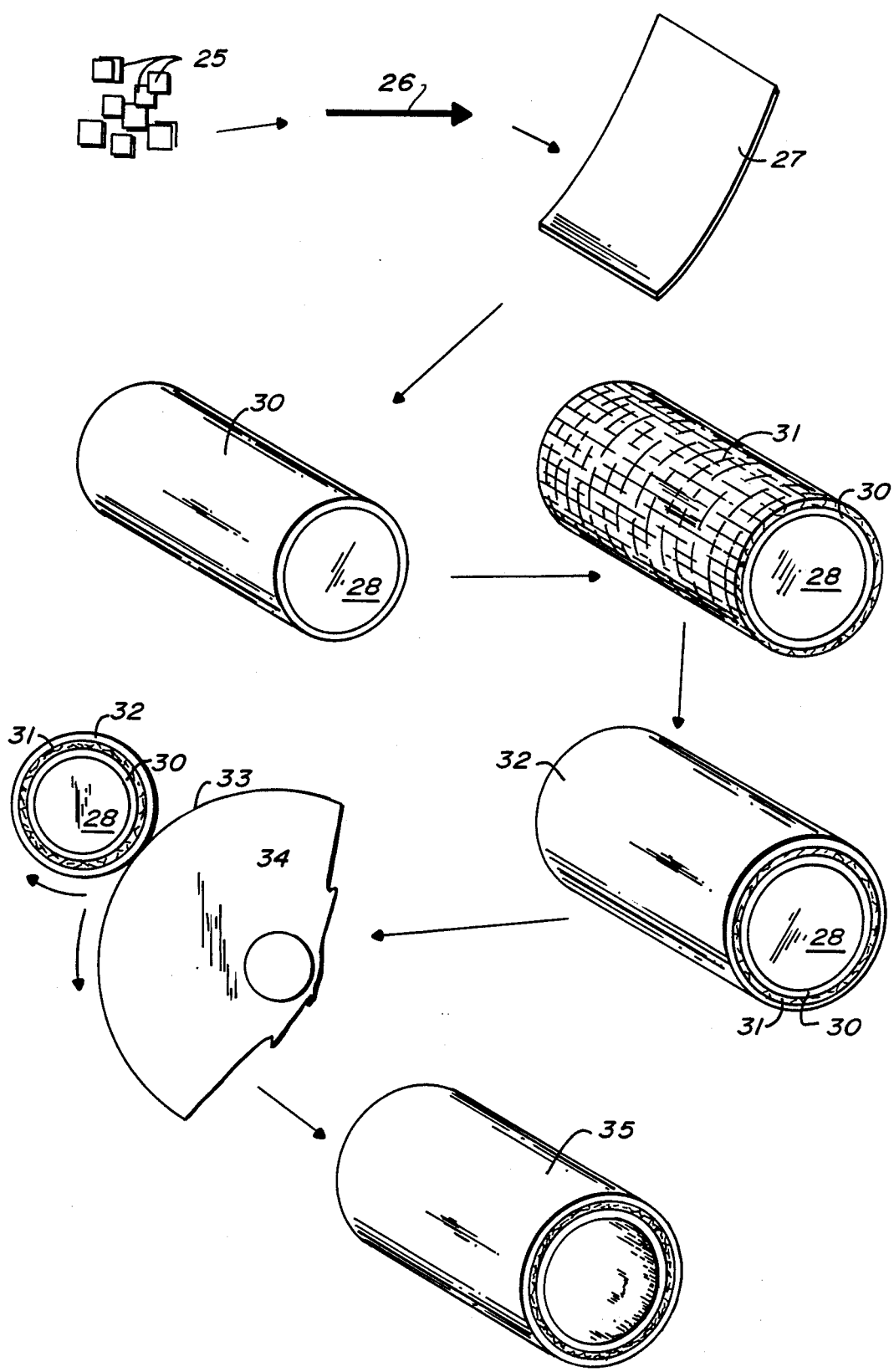
FIG. 6 is a flow sheet with diagrammatic views of each step in a process embodying the invention for making a tubular composite product.

Single-phase composites of this invention can be made by using an ultra-high-molecular-weight polymer such as UHMWPE and applying it as a pseudo-gel in a volatile (e.g., Decalin) or non-volatile (e.g., paraffin oil) solvent on a single- or plural-layer fibrillar structure (such as high-modulus high-strength fibers or ribbons laid in orderly manner or dispersed randomly), of the same polymer resin (e.g., UHMWPE) or from polymer resins with identical or similar properties prior to their processing into the matrix and fiber forms, in a temperature range in general between room temperature and the melting point of the UHMWPE high-modulus fibers or ribbons of approximately 140°-145° C. (and preferably between the dissolution temperature of the crystalline morphologies (about 120° C.) in the UHMWPE pseudo-gel and 130° C.), and subsequently cooling the composite system to below the gelation temperature of the pseudo-gel (approximately 120° C.) under compression of approximately 1000-5000 psi. When applying the pseudo-gel at temperatures above 130° C., the filaments should be under tension, to prevent shrinkage of the fibers.

Unlike the prior-art transcrystallization process which involves the crystal growth of the matrix upon its melt crystallization perpendicular to the direction of the reinforcing fibers, the present invention uses gelation of the matrix on the fibers that involves the generation of randomly oriented stacks of single crystals and "shish kebab" crystals and their deposition onto and around the crystalline reinforcing fibers.

Thus, FIG. 1 shows the UHMWPE matrix deposited onto the crystalline reinforcing fibers. The fibers have a crystalline lamellar structure perpendicular to the fiber direction.

FIG. 2 shows shish-kebab crystals of the UHMWPE matrix deposited onto the crystalline lamellar structure perpendicular to the direction of the reinforcing fibers.

FIG. 3 shows two adjacent and aligned reinforcing fibers partially coated with UHMWPE matrix.

The composite may be a flat sheet, a tube, or a solid rod.

Thus, FIG. 4 shows two UHMWPE pseudo-gel sheets 10 and 11 with a knitted fibrillar structure 12 sandwiched between them. The fibers of the structure 12 are also made of UHMWPE.

FIG. 5 similarly shows, exploded, a multilayer composite structure made up of four UHMWPE pseudo-gel sheets 15, 16, 17, and 18 with three knitted fibrillar structures 20, 21, and 22 successively sandwiched between them.

The compression process can take place in a continuous or non-continuous process, as practiced in a rolling or compression molding, and other alternatives are also available. Subsequently, the solvent can be removed from the matrix of the composite by simple evaporation, in the case of the volatile solvent, such as Decalin (decahydronaphthalene), or extraction with a suitable solvent (e.g., hexane) in the case of the non-volatile solvent (paraffin oil). The reinforcing fibers in the composite can be continuous or short, and can be knitted, woven, randomly dispersed or otherwise used.

The so obtained "UHMWPE gel coated" fibrillar reinforcements of UHMWPE can be prepared in single or more layers by superimposing the single layers and compressing the entire assembly into a single or a multilayer composite structure and then evaporating the volatile solvent or extracting the non-volatile solvent with a suitable solvent as in the case of the single layer composites. Alternatively, the UHMWPE fibrillar reinforcements can be commingled in the UHMWPE pseudo-gel so that when the solvent is removed (either by evaporation or extraction depending on the solvent) a single phase composite of randomly dispersed UHMWPE fibers in UHMWPE matrix is obtained.

Other polymers that may be processed into such one-phase composite products in which the matrix and the reinforcing fibers are made of the same polymer, as defined in this specification, include isotactic polypropylene, poly(ethylene terephthalate), polyamides, poly(vinyl alcohol), polyacrylonitrile, and other linear polymers with sufficiently high molecular weight or polar groups in their chain backbone so that they can form a pseudo-gel state of the type described in the mother patent and capable of deforming into high-modulus, high-strength fibrillar products. In their filamentary form, these linear polymers may be as single-strand fibers, multi-strand fibers, or ribbons. The filaments may be long or chopped, randomly dispersed or texturized, knitted, woven, or braided.

EXAMPLE 1

In one experiment, a UHMWPE (Hercules HiFax 1900, $M_w \geq 3.2 \times 10^6$) gel (5% UHMWPE in 95% paraffin oil, by weight) was heated to 125° C. and applied to a woven UHMWPE (Hercules HiFax 1900, $M_w 3.2 \times 10^6$) high-modulus-strength-structure on either side. The so coated woven structure was then placed under compression at about 2,000 psi at 125° C. The temperature was lowered subsequently to at least about 100° C., and the gel-coated UHMWPE knitted structure with high modulus and high strength was retrieved. This composite system was then placed in an extractor to extract the non-volatile paraffin oil with hexane, which was removed from the composite by evaporation to obtain the single phase composite of woven UHMWPE fibers in UHMWPE matrix.

EXAMPLE 2

In an independent experiment, a UHMWPE (American Hoescht-Celanese, Hostalen GUR-412, $M_w \sim 3.3 \times 10^6$) gel (5% UHMWPE in 95% paraffin oil, by weight) was heated to 125° C. and applied to a woven UHMWPE (Hercules HiFax 1900, $M_w \geq 3.2 \times 10^6$) high-modulus, high-strength structure on either side. The so-coated woven structure was processed under the same procedure as in Example 1 to obtain a single-phase composite of woven UHMWPE fibers in a UHMWPE matrix of different UHMWPE origin.

EXAMPLE 3

In another independent experiment, a UHMWPE (American Hoescht-Celanese, Hostalen GUR-412, $M_w \sim 3.3 \times 10^6$) gel (5% UHMWPE in 95% paraffin oil) was heated 125° C. and applied to UHMWPE (Mitsubishi Hizex Million 240 M, $M_v = 2 \times 10^6$) high-modulus, high-strength fibers which were aligned uniaxially. The so coated uniaxial structure was processed under the same procedure as in Example 1 to obtain a single phase composite of uniaxially aligned UHMWPE fibers in a UHMWPE of different UHMWPE origin.

EXAMPLE 4

The same procedure was followed with the multi-layer composite structure. The UHMWPE (Hercules HiFax 1900, $M_w \geq 3.2 \times 10^6$) gel-coated UHMWPE (Hercules HiFax 1900, $M_w \geq 3.2 \times 10^6$) woven layers were superimposed and the assembly was compressed and subsequently treated as described above for the single-layer structure in Example 1.

EXAMPLE 5

In one particular experiment, an UHMWPE (Hercules HiFax 1900, $M_w \geq 3.2 \times 10^6$) paraffin oil pseudo-gel (4% w/w) was heated to 118° C. (at this temperature the pseudo-gel turned into a viscous fluid) and was applied on a woven UHMWPE (Hercules HiFax 1900, $M_w \geq 3.2 \times 10^6$) fibrillar structure by merging the latter into a thin layer of the former. (A woven UHMWPE fibrillar structure may be coated on one or both sides depending on the spacing between the knitted fibrils.) Subsequently, the structure was processed by compression molding in one case and, in another, passed between compression rolls and cooled until the viscous coating became an opaque pseudo-gel (at $T \geq 118°$ C.). Thereafter, the solvent was removed from the pseudo-gel coating by the extraction methodology described above for the single-layer structure.

EXAMPLE 6

In another experiment, a UHMWPE (American Hoescht-Celanese, Hostalen GUR-412, $M_w \sim 3.3 \times 10^6$) gel (5% w/w UHMWPE in paraffin oil) was heated to 125°

C. Then, randomly oriented and dispersed UHMWPE fibers (Hercules HiFax 1900, $M_w \geq 3.2 \times 10^6$) were commingled in it and the system was placed under compression at about 2000 psi at 125° C. The temperature was decreased subsequently to at least about 100° C. and a UHMWPE gel-coated "mesh" of randomly dispersed high-modulus and high-strength fibers of UHMWPE was obtained. This system was then placed in an extractor to extract the paraffin oil with hexane, which was removed from the composite by evaporation to obtain a single phase composite of randomly mixed UHMWPE high modulus and strength fibers in UHMWPE.

EXAMPLE 7

For a multilayer composite structure, for example, a composite structure with five layers of UHMWPE woven fibrillar structures, the coated UHMWPE woven fibrils with UHMWPE pseudo-gel were superimposed and compression molded at 120° C. The multilayer composite systems were then placed in an extractor to extract the non-volatile paraffin oil with hexane, which was removed from the composite by evaporation.

EXAMPLE 8

An alternative methodology for the preparation of the single-phase composites involves the stacking of thin UHMWPE pseudo-gel films between alternating UHMWPE knitted fibrillar layers for the preparation of multilayer composites or the use of the thin pseudo-gel films to "sandwich" a single UHMWPE knitted fibrillar layer for the preparation of a composite with a single fibrillar layer as shown in FIG. 4. The thin UHMWPE pseudo-gel films were obtained according to the processing methodology involving the first two steps of FIG. 6, in which pieces 25 of the UHMWPE pseudo-gel (UHMWPE/paraffin oil 5% weight, by weight) are compressed at 26 to make a gel-like sheet 27. The assemblies of the thin gel film and knitted structure(s) were compression molded at approximately 123° C. and retrieved after cooling to below 120° C. for the removal of the non-volatile solvent as mentioned above.

EXAMPLE 9

A tubular composite structure with a "sandwiched" UHMWPE fibrillar layer between thin UHMWPE pseudo-gel films were obtained by the process of FIG. 6. Pieces 25 of the pseudo-gel are compressed at step 26 to make a gel-like sheet 27. The sheet 27 is wrapped around a mandrel 28 to produce a gel-like tube 30. Then a tubular UHMWPE fibrillar woven or knitted structure 31 is passed on to the gel-like tube 30, and an additional gel-like sheet 32 is wrapped on top of the UHMWPE fibrillar woven or knitted structure 31, and the assembly is compression rolled against an adjacent rolling surface 33 of a roller 34 at approximately 120° C. Depending on the size of the interstices or texturization of the weaving or knit pattern, the outside UHMWPE gel-sheet 32 may not be required, as the inner layer 30 may exude through the fibrils of the middle woven or knitted layer 31 and thus allow for a uniform coating on both sides. After cooling the so-prepared tubular samples to below 120° C., they were retrieved for the removal of the non-volatile solvent as described above, to give a tubular product 35.

EXAMPLE 10

Alternative methodologies involving the continuous gel coating of a sheet or a tubular knitted or woven UHMWPE fibrillar structure can be used also. FIG. 7 is a schematic of a continuous process for the preparation of single-phase sheet composites of UHMWPE. A knitted or woven fibrillar structure 40 is fed from a mandrel 41 to a gel-coating zone 42. The resulting gel coated fibrillar structure 43 is passed through between cooling and compression rolls 44 and 45 (a plurality of rolls may be used also) to form a composite 46, which after the extraction 47 of the non-volatile solvent gives a flat composite structure 48. Such a composite structure 48 can be treated thermally and/or under compression in step 49 to a final product 50.

Such systems (single-phase composites) may combine the physical properties, e.g., transport properties of the isotropic matrix and the high mechanical performance of the same polymer with a fibrillar structure, e.g., in knitted Dacron arterial prostheses, the porosity of the tubular knitted structure can be controlled beyond the present limits of adjustment by thread size or interstices size or texturization of the knit pattern, by the concentration and thickness of the poly(ethylene terephthalate) pseudo-gel coating on the knitted tubular prosthesis.

Similarly, in the UHMWPE "arterial" prostheses based on a knitted UHMWPE tubular structure and a pseudo-gel coating of the parent and this patent application, the porosity of the arterial prostheses can be controlled by the concentration and thickness of the UHMWPE pseudo-gel coating on the knitted tubular device and by adjustment of the thread size or interstices size or texturization of the knitted pattern.

EXAMPLE 11

Another methodology of continuous production of a single-phase composite of UHMWPE in sheet form involves the formation of a gel-coated mesh of randomly dispersed and oriented UHMWPE fibers by commingling the UHMWPE fibers in a UHMWPE pseudo-gel heated to a temperature close to but above its gelation temperature and its subsequent cooling and compression through a set of cooling and compression rolls. This composite mesh structure is then taken to an extraction step to remove the paraffin oil with hexane which is removed from the composite by evaporation. The product is a single-phase composite sheet comprised of a mesh of UHMWPE high-modulus and high-strength fibers in UHMWPE.

Similar structural configurations of single phase composites can be obtained with other polymers such as polypropylene, poly(vinyl alcohol), polyamides, and polyesters.

Isotactic polypropylene ($M_v \sim 3.4 \times 10^6$) can be dissolved in decalin (for example, 1% w/v) at approximately 185° C. in the presence of an antioxidant such as Irgonox-1076 (Ciba-Geigy Co.) (0.5% w/w of the polymer) and form a pseudo gel state by cooling to a temperature of $\leq 90°$ C. Such a pseudo-gel can be applied onto high-modulus and high-strength fibers of isotactic polypropylene produced by spinning or solid state deformation processes, by the processing methodology described above to obtain a structure of polypropylene coated polypropylene fibers. The solvent can be removed from these structures to some extent by compression or by vacuum removal. The fibers can be in the form of monofilaments, they can be long or short and in knitted, woven, braided, or randomly dispersed structures. The dried composite can be processed further, as described above.

Alternatively, isotactic polypropylene can be dissolved in paraffin oil (for example, 6% w/w) at about 200° C. and form a pseudo-gel by cooling to ≦90° C. In this case (i.e., when a non-volatile solvent is used) after the polypropylene is applied onto the polypropylene fibers, the paraffin oil can be extracted with a solvent such as trichlorotrifluroethane which subsequently can be removed by evaporation.

Poly(vinyl alcohol) ($\overline{M}_w$=150,000) can be dissolved in a 2:1 ethylene glycol and water mixture (for example 4% w/w) at 135° C. and form a pseudo-gel by cooling to ambient temperature. The poly(vinyl alcohol) can be applied onto poly(vinyl alcohol) high-modulus and high-strength structure as described above. The solvent system can be removed from the composite by compression or vacuum removal. Again, the poly(vinyl alcohol) high-modulus and high-strength fibers can be in different forms and patterns or be randomly dispersed as described above.

Nylon 6 ($M_v$~180,000) can be dissolved in benzyl alcohol (for example 5% w/w) at approximately 165° C. and form a pseudo-gel on cooling to ambient temperature. The Nylon 6 pseudo-gel can be applied onto melt-spun Nylon 6 fibers, as described above. The Nylon 6 fibers in the single-phase composite can be in different forms and patterns or randomly dispersed. The solvent can be removed from the composite by compression and/or vacuum removal.

Poly(ethylene terephthalate) ($M_v$~100,000) can be dissolved in nitrobenzene (for example, 10% w/w) and form a pseudo-gel on cooling to ambient temperature. Such a pseudo-gel can be applied onto melt spun or otherwise produced poly(ethylene terephthalate) high-modulus and high-strength fibers to form a single phase composite using the process described above.

EXAMPLE 12

A methodology for the preparation of single-phase composite in the form of solid rods, involves the immersion of a braided UHMWPE structure of high-modulus and high-strength fibers into a UHMWPE pseudo-gel heated to a temperature close to but above its gelation temperature and its subsequent cooling and compression through a converging die geometry or compression mold. The composite is then taken to an extraction step and/or evaporation step as described above to obtain a single phase composite using a braided UHMWPE structure of high-modulus and high-strength fibers.

EXAMPLE 13

An alternative methodology for the preparation of a single phase composite in the form of a solid rod uses the same steps described for the sheet laminate structures apart that the laminates of the UHMWPE pseudo-gel and the UHMWPE knitted or woven structures are rolled tightly and compressed into a solid rod which subsequently is taken to an extraction and/or evaporation step, as described above, to obtain a single-phase composite having a circular laminated structure.

Since, when making a solid rod with a thick cross-sectional area using the methodology explained above, it is time consuming to remove a non-volatile solvent by extraction, the use of a volatile solvent is preferable, for it can be removed more readily by evaporation.

In addition to the biomedical uses suggested in this patent application there are numerous other applications, which include tendons, ligaments, porous membranes, screens, high pressure vessels and pipes, ballistic applications and structural components.

To those skilled in the art to which this invention relates, many changes in construction and widely differing embodiments and applications of the invention will suggest themselves without departing from the spirit and scope of the invention. Such embodiments may include the fabrication of single-phase composite systems in which the fibers are dispersed randomly or laid in some particular pattern, the fabrication of single composites in which the fibers are short or long, the fabrication of composites in which the polymer matrix which is capable of gelling and the polymer fiber reinforcements are compatible, the fabrication of composites in which the polymer matrix is filled with additives or blended with compatible polymers for the purpose of e.g., enhancing its adhesion, and the fabrication of laminate structures incorporating such single phase polymer composites and metal sheets.

A few examples of such embodiments are the fabrication of a composite structure comprised of, e.g., an isotactic polypropylene matrix and UHMWPE fibers. The isotactic polypropylene forms in decalin a pseudo-gel by cooling to ≦90° C. and hence it can be applied on the UHMWPE fibers without affecting its mechanical properties. Similarly, a polyamide forms a pseudo-gel (e.g. Nylon 6 in nitrobenzene) on cooling to ambient temperature and can be applied onto UHMWPE fibers. The disclosures and the descriptions herein are purely illustrative and are not intended to be in any sense limiting.

What is claimed is:

1. A single phase composite structure of a filamentary reinforcing component and a non-filamentary matrix component made from the same semicrystalline linear polymer with a weight average molecular weight of at least 500,000, which is capable of forming a pseudo-gel in a solvent compatible with forming such pseudo-gel and of being processed into a high modulus, and high strength fibrillar product with a tensile modulus of at least 10 GPa and a tensile strength of at least 0.5 GPa, said composite structure comprising:

layers of the non-filamentary matrix component of said polymer in sheet form interleaved with at least one layer of the filamentary reinforcing component, also of said polymer, comprised of high modulus, high strength fibers.

2. The structure of claim 1 wherein there is a single filamentary reinforcing layer of high-modulus, high strength fibers and two sheet layers of the matrix.

3. The structure of claim 1 wherein there are a plurality of filamentary layers of high modulus, high strength fibers and a plurality of sheet layers of matrix.

4. The structure of claim 1 wherein said structure is flat in the form of a sheet.

5. The structure of claim 1 wherein said structure is in the form of a tube.

6. The structure of claim 1 wherein said structure is in the form of a solid rod.

7. The structure of claim 1 wherein said polymer is ultra-high-molecular-weight polyethylene.

8. The structure of claim 1 wherein said polymer is selected from the group consisting of ultra-high-molecular-weight polyethylene, isotactic polypropylene, poly(L-lactide), poly(vinyl alcohol), polyacrylonitrile, poly(ethylene terephthalate), and polyamides.

9. The structure of claim 8 wherein said polymers are selected so as to form a pseudo-gel with a solvent selected from the group consisting of Decalin or paraffin oil for the polyethylene, Decalin or paraffin oil for polypropylene, chloroform for poly(L-lactide), ethylene glycol and water for poly(vinyl alcohol), methyl formamide or tetramethylene sulfone for polyacrylonitrile, nitrobenzene for poly(ethylene terephthalate), and benzyl alcohol for polyamides.

10. The composite of claim 9 wherein the non-filamentary matrix component is interleaved in sheet form with at least one layer of the reinforcing fibrillar component.

11. The composite of claim 9 wherein there is a plurality of reinforcing fibrillar layers and a plurality of sheet layers of non-filamentary matrix.

12. The composite of claim 9 wherein the reinforcing fibrillar component is randomly dispersed in the non-filamentary matrix component.

13. The structure of claim 9 wherein said structure is flat and in the form of a sheet.

14. The structure of claim 9 wherein said structure is in the form of a tube.

15. The structure of claim 9 wherein said structure is in the form of a solid rod.

16. The structure of claim 9 wherein said polymer is ultra-high-molecular-weight polyethylene having a relative viscosity of 2.3 or greater, at a solution concentration of 0.05% at 135° C. in decahydronaphthalene.

17. The structure of claim 9 wherein said polymer is selected from the group consisting of polyethylene, isotactic polypropylene, poly(L-lactide), poly(vinyl alcohol), polyacrylonitrile, poly(ethylene terephthalate), and polyamides.

* * * * *